(12) United States Patent
Stowe et al.

(10) Patent No.: US 8,823,942 B1
(45) Date of Patent: Sep. 2, 2014

(54) ENVIRONMENTAL CELL ASSEMBLY FOR USE IN FOR USE IN SPECTROSCOPY AND MICROSCOPY APPLICATIONS

(71) Applicants: Ashley Clinton Stowe, Knoxville, TN (US); Norman Smyrl, Knoxville, TN (US); Russell L. Hallman, Jr., Knoxville, TN (US)

(72) Inventors: Ashley Clinton Stowe, Knoxville, TN (US); Norman Smyrl, Knoxville, TN (US); Russell L. Hallman, Jr., Knoxville, TN (US)

(73) Assignee: Consolidated Nuclear Security, LLC, Oak Ridge, TN (US)

( * ) Notice: Subject to any disclaimer, the term of this patent is extended or adjusted under 35 U.S.C. 154(b) by 0 days.

(21) Appl. No.: 13/835,005

(22) Filed: Mar. 15, 2013

(51) Int. Cl.
*G01N 21/00* (2006.01)
*G01N 1/10* (2006.01)

(52) U.S. Cl.
USPC ....... 356/440; 256/319; 256/246; 250/339.07

(58) Field of Classification Search
USPC ................. 356/244, 246, 432–440, 301, 319; 250/339.07
See application file for complete search history.

(56) References Cited

U.S. PATENT DOCUMENTS

| | | | |
|---|---|---|---|
| 5,166,743 A * | 11/1992 | Garner | 356/73 |
| 7,255,474 B2 | 8/2007 | Cong et al. | |
| 8,309,929 B2 | 11/2012 | Bond et al. | |
| 2005/0207005 A1 * | 9/2005 | Kawano | 359/388 |
| 2011/0102572 A1 * | 5/2011 | Kihara et al. | 348/79 |

* cited by examiner

*Primary Examiner* — Hoa Pham
(74) *Attorney, Agent, or Firm* — Clements Bernard PLLC; Christopher L. Bernard; Lawrence A. Baratta, Jr.

(57) ABSTRACT

An environmental cell assembly for use in microscopy and spectroscopy applications, including: an environmentally sealed body assembly configured to selectively hold and contain a sample; a plurality of ports manufactured into one or more surfaces of the body assembly for one or more of evacuating the body assembly and injecting a gas into or removing a gas from the body assembly; a port manufactured into a surface of the body assembly for receiving a translating stage configured to move the sample within the body assembly; and a port manufactured into a surface of the body assembly for receiving one or more lenses utilized in a microscopy or spectroscopy application; wherein the one or more lenses are disposed adjacent the sample without intervening structures disposed there between. The cell assembly also includes a port manufactured into a surface of the body assembly for retaining a window and providing visualization of the sample.

19 Claims, 4 Drawing Sheets

ENVIRONMENTAL CELL ASSEMBLY FOR USE IN FOR USE IN SPECTROSCOPY AND MICROSCOPY APPLICATIONS

STATEMENT REGARDING FEDERALLY SPONSORED RESEARCH OR DEVELOPMENT

The U.S. Government has rights to the present disclosure pursuant to Contract No. AC05-00OR22800 between the U.S. Department of Energy and Babcock and Wilcox Technical Services Y-12, LLC.

FIELD OF THE DISCLOSURE

The present disclosure relates generally to the microscopy and spectroscopy fields. More specifically, the present disclosure relates to an environmental cell assembly for use in microscopy and spectroscopy applications, especially those involving samples that are very air sensitive, reactive, and/or that possess very weak Raman signatures.

BACKGROUND OF THE DISCLOSURE

Some samples, such as metal hydrides, for example, are very air sensitive and possess very weak Raman signatures. As such microscopy and spectroscopy methods that utilize a conventional window material (e.g. glass, quartz, or the like) between the sample and the objective lens(es) can attenuate the Raman signal(s) by a factor of up to ten. Such conventional window materials are typically necessary such that the environmental cell assembly utilized can be evacuated and/or purged, and, optionally, a reactive gas can be introduced in a controlled manner. In other words, the sample must be protected from the outside environment. This is problematic.

Thus, what is needed in the art is an environmental cell assembly that does not incorporate a conventional window material between the sample and the objective lens(es) of a microscope or spectroscopic assembly, such that the Raman signal(s) are not significantly attenuated. This environmental cell assembly should allow for the vertical, and potentially the horizontal and rotational, adjustment of the position of the sample within the environmental cell assembly, as well as the ready evacuation of the environmental cell assembly, the introduction of a purge (i.e. inert) gas, the introduction of a reactive gas, etc. In other words, the environmental cell assembly should provide the sample with isolation from the outside environment while microscope and/or spectroscopic methodologies are employed. By meeting all of these criteria, even very weak Raman signals can be detected and utilized in further analyses.

BRIEF SUMMARY OF THE DISCLOSURE

In various exemplary embodiments, the present disclosure provides such an environmental cell assembly that does not incorporate a conventional window material between the sample and the objective lens(es) of a microscope or spectroscopic assembly, such that the Raman signal(s) are not significantly attenuated. This environmental cell assembly allows for the vertical, and optionally the horizontal and rotational, adjustment of the position of the sample within the environmental cell assembly, as well as the ready evacuation of the environmental cell assembly, the introduction of a purge (i.e. inert) gas, the introduction of a reactive gas, etc. In other words, the environmental cell assembly provides the sample with isolation from the outside environment while microscope and/or spectroscopic methodologies are employed. By meeting all of these criteria, even very weak Raman signals can be detected and utilized in further analyses. The objective lens(es) of the environmental cell assembly of the present disclosure can be coupled to any conventional microscopes and/or optical or laser spectroscopy equipment.

In one exemplary embodiment, the present invention provides an environmental cell assembly for use in microscopy and spectroscopy applications, including: an environmentally sealed body assembly configured to selectively hold and contain a sample; a plurality of ports manufactured into one or more surfaces of the environmentally sealed body assembly for one or more of evacuating the environmentally sealed body assembly and injecting a gas into or removing a gas from the environmentally sealed body assembly; a port manufactured into a surface of the environmentally sealed body assembly for receiving a translating stage configured to move the sample within the environmentally sealed body assembly; and a port manufactured into a surface of the environmentally sealed body assembly for receiving one or more lenses utilized in a microscopy or spectroscopy application; wherein the one or more lenses are disposed adjacent the sample without intervening structures disposed there between. The environmental cell assembly also includes a port manufactured into a surface of the environmentally sealed body assembly for retaining a window and providing visualization of the sample. Optionally, the environmentally sealed body assembly includes a plurality of sides that are one or more of fixedly attached to one another and integrally formed with one another. The translating stage is operable for moving the sample vertically within the environmentally sealed body assembly. Optionally, the translating stage is also operable for moving the sample horizontally within the environmentally sealed body assembly. Optionally, the environmental cell assembly further includes a heating device disposed within or adjacent and in thermal communication with or through the environmentally sealed body assembly for selectively heating the sample. Optionally, the environmental cell assembly still further includes a sample holding device selectively disposed within the environmentally sealed body assembly.

In another exemplary embodiment, the present invention provides a method for providing an environmental cell assembly for use in microscopy and spectroscopy applications, including: providing an environmentally sealed body assembly configured to selectively hold and contain a sample; providing a plurality of ports manufactured into one or more surfaces of the environmentally sealed body assembly for one or more of evacuating the environmentally sealed body assembly and injecting a gas into or removing a gas from the environmentally sealed body assembly; providing a port manufactured into a surface of the environmentally sealed body assembly for receiving a translating stage configured to move the sample within the environmentally sealed body assembly; and providing a port manufactured into a surface of the environmentally sealed body assembly for receiving one or more lenses utilized in a microscopy or spectroscopy application; wherein the one or more lenses are disposed adjacent the sample without intervening structures disposed there between. The method also includes providing a port manufactured into a surface of the environmentally sealed body assembly for retaining a window and providing visualization of the sample. Optionally, the environmentally sealed body assembly includes a plurality of sides that are one or more of fixedly attached to one another and integrally formed with one another. The translating stage is operable for moving the sample vertically within the environmentally sealed body assembly. Optionally, the translating stage is operable for moving the sample horizontally within the environmentally sealed body assembly. Optionally, the method further includes providing a heating device disposed within or adjacent and in thermal communication with or through the environmentally sealed body assembly for selectively heating the sample. Optionally, the method still further includes providing a sample holding device selectively disposed within the environmentally sealed body assembly.

In a further exemplary embodiment, the present invention provides an environmental cell assembly for use in microscopy and spectroscopy applications, including: an environmentally sealed body assembly configured to selectively hold and contain a sample; a plurality of ports manufactured into one or more surfaces of the environmentally sealed body assembly for one or more of evacuating the environmentally sealed body assembly and injecting a gas into or removing a gas from the environmentally sealed body assembly; a port manufactured into a surface of the environmentally sealed body assembly for receiving a translating stage configured to move the sample within the environmentally sealed body assembly; and a port manufactured into a surface of the environmentally sealed body assembly for receiving an objective utilized in a microscopy or spectroscopy application, wherein at least a portion of the objective protrudes into the environmentally sealed body assembly; wherein the one or more lenses are disposed adjacent the sample without intervening structures disposed there between. The environmental cell assembly also includes a port manufactured into a surface of the environmentally sealed body assembly for retaining a window and providing visualization of the sample. Optionally, the environmentally sealed body assembly includes a plurality of sides that are one or more of fixedly attached to one another and integrally formed with one another. Optionally, the environmental cell assembly further includes a heating device disposed within or adjacent and in thermal communication with or through the environmentally sealed body assembly for selectively heating the sample. Optionally, the environmental cell assembly still further includes a sample holding device selectively disposed within the environmentally sealed body assembly.

BRIEF DESCRIPTION OF THE DRAWINGS

The present disclosure is illustrated and described herein with reference to the various drawings, in which like reference numbers are used to denote like assembly components/ method steps, as appropriate, and in which.

DETAILED DESCRIPTION OF THE DISCLOSURE

Figure 1:
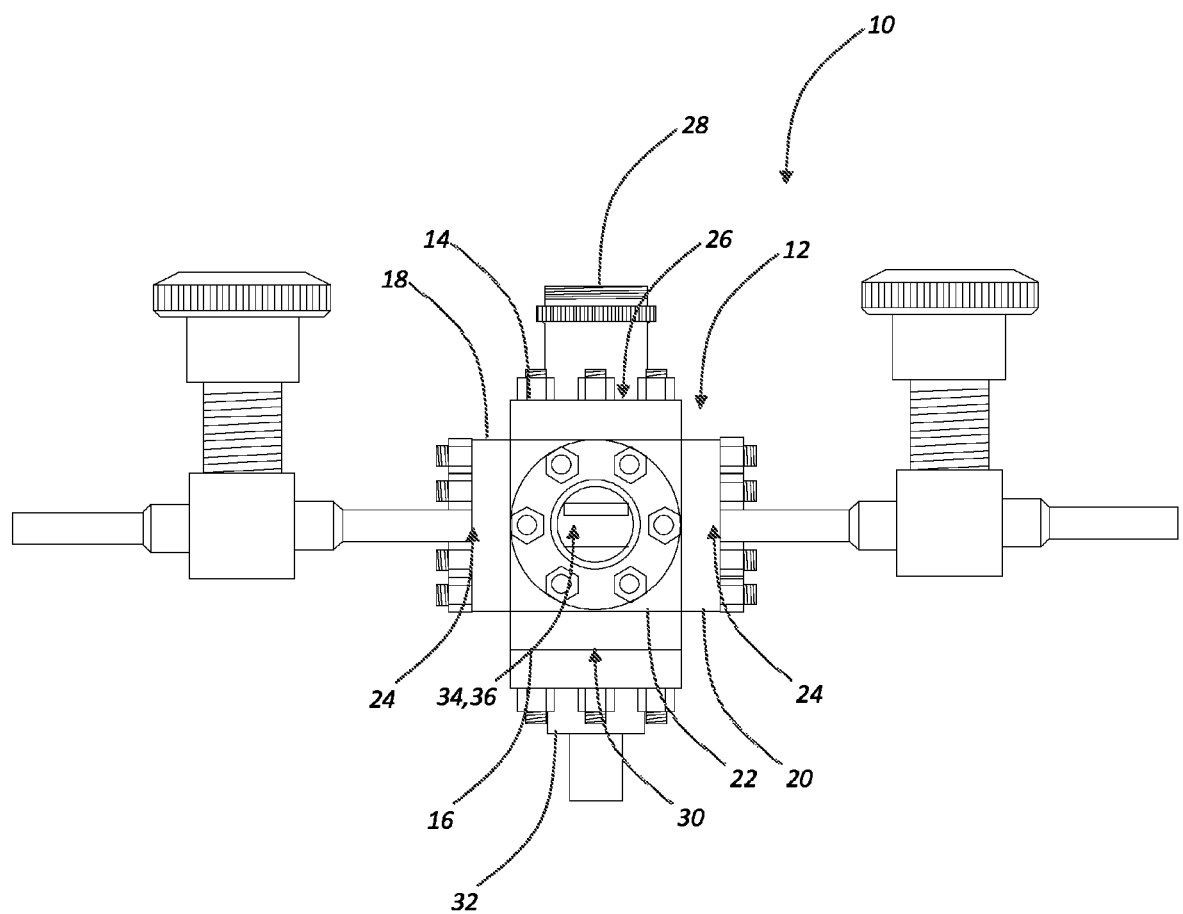
FIG. 1 is a planar side view of one exemplary embodiment of the environmental cell assembly of the present disclosure in an assembled state.
Figure 2:
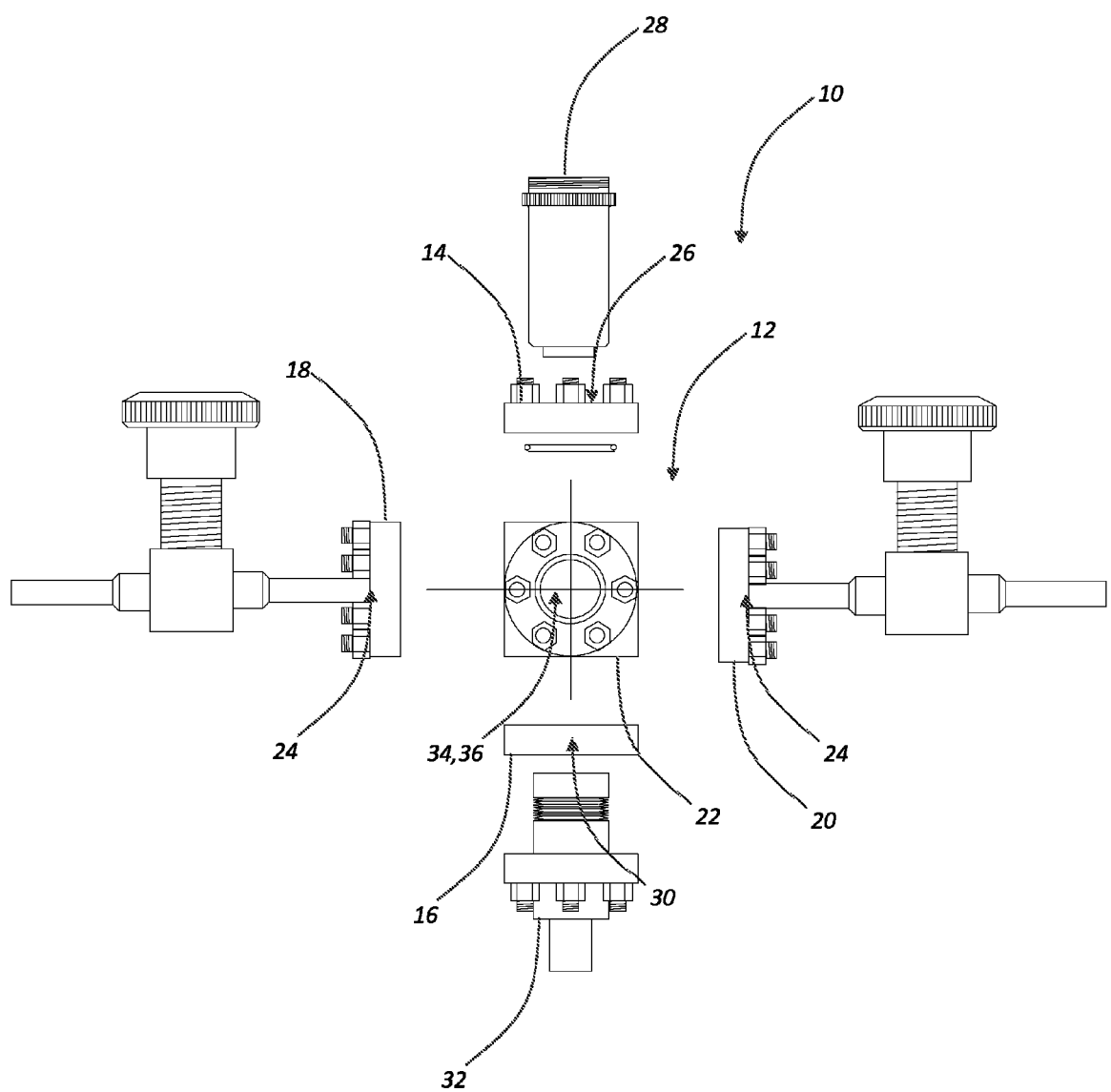
FIG. 2 is an exploded planar side view of one exemplary embodiment of the environmental cell assembly of the present disclosure in a partially unassembled state.

Referring specifically to FIGS. 1 and 2, in one exemplary embodiment, the environmental cell assembly 10 of the present disclosure takes the form of an environmentally-sealed cube or other shape (when assembled). Thus, the environmental cell assembly 10 includes an environmentally-sealed body assembly 12, having six sides in the embodiment illustrated, but which can also have a smaller or larger number of sides, including partially or wholly convex or concave sides. In the exemplary embodiment illustrated, the environmentally-sealed body assembly 12 includes a top side 14, a bottom side 16, a left side 18, a right side 20, a front side 22, and a back side (not illustrated). These sides can be bolted together and/or otherwise securely joined to form a unitary body. Any number of fluidly-transmissive ports, mechanically-transmissive ports, and/or visual-transmissive ports can be manufactured through the sides of the environmentally-sealed body assembly 12.

In the exemplary embodiment illustrated, these ports include two ports 24 manufactured through the left side 18 and the right side 20 of the body assembly 12 for the evacuation of the body assembly 12, and/or the introduction of purge and/or reactive gasses. These ports 24 are coupled to appropriate conduits, valve assemblies, control systems, and pumps, not especially relevant to the present disclosure. Appropriate connections, welds, and/or seals are utilized to ensure environmental isolation. The ports also include one port 26 manufactured through the top side 14 of the body assembly 12 through which an environmentally-sealed objective 28 is sealingly disposed, such that the objective 28 is in direct optical or radiative communication with the sample (not illustrated) disposed within the body assembly 12. Again, appropriate connections, welds, and/or seals are utilized to ensure environmental isolation. The ports further include one port 30 manufactured through the bottom side 16 of the body assembly 12 through which a translating stage 32 is sealingly disposed, such that the translating stage 32 is in direct mechanical communication with the sample disposed within the body assembly 12. Again, appropriate connections, welds, and/or seals are utilized to ensure environmental isolation. Finally, the ports include one port 34 manufactured through the front side 22 and/or back side of the body assembly 12 in which a visualization window 36 is sealingly disposed, such that visualization of the sample disposed within the body assembly 12 is possible. Again, appropriate connections, welds, and/or seals are utilized to ensure environmental isolation.

The objective 28 includes any conventional objective suitable for microscope and/or spectroscopic applications, provided that the objective 28 is in direct optical or radiative communication with the sample, with only intervening atmosphere there between within the interior of the body assembly 12.

The translating stage 32 can be any conventional translating stage that is capable of moving the sample vertically and/or horizontally within the interior of the body assembly 12. Any suitable sample holding devices can be coupled to or disposed on a portion of the translating stage 32, thereby holding the sample securely in place within the body assembly 12.

The visualization window 36 can be partially or wholly comprised of any visual-transmissive material (e.g. glass, quartz, or the like), such that the sample can be visualized there through.

All of the metallic components of the body assembly, etc., can be made of stainless steel, Aluminum, and/or the like. Seals can be made of Indium, Copper, Aluminum, and/or the like. It should be noted that the use of Aluminum has the advantage of eliminating Hydrogen outgassing in those applications that are Hydrogen sensitive. In general, the choice of appropriate materials will be appreciated by those of ordinary skill in the art, based on their heat-transmissive or insulative properties, as required in the given instance.

In another exemplary embodiment, a plate heater or the like (not illustrated) can be disposed between the translating stage 32 and the sample. Other means for heating the sample can also be utilized, with a heater thermally coupled to various components of the body assembly 12, given the specific application.

Figure 3:
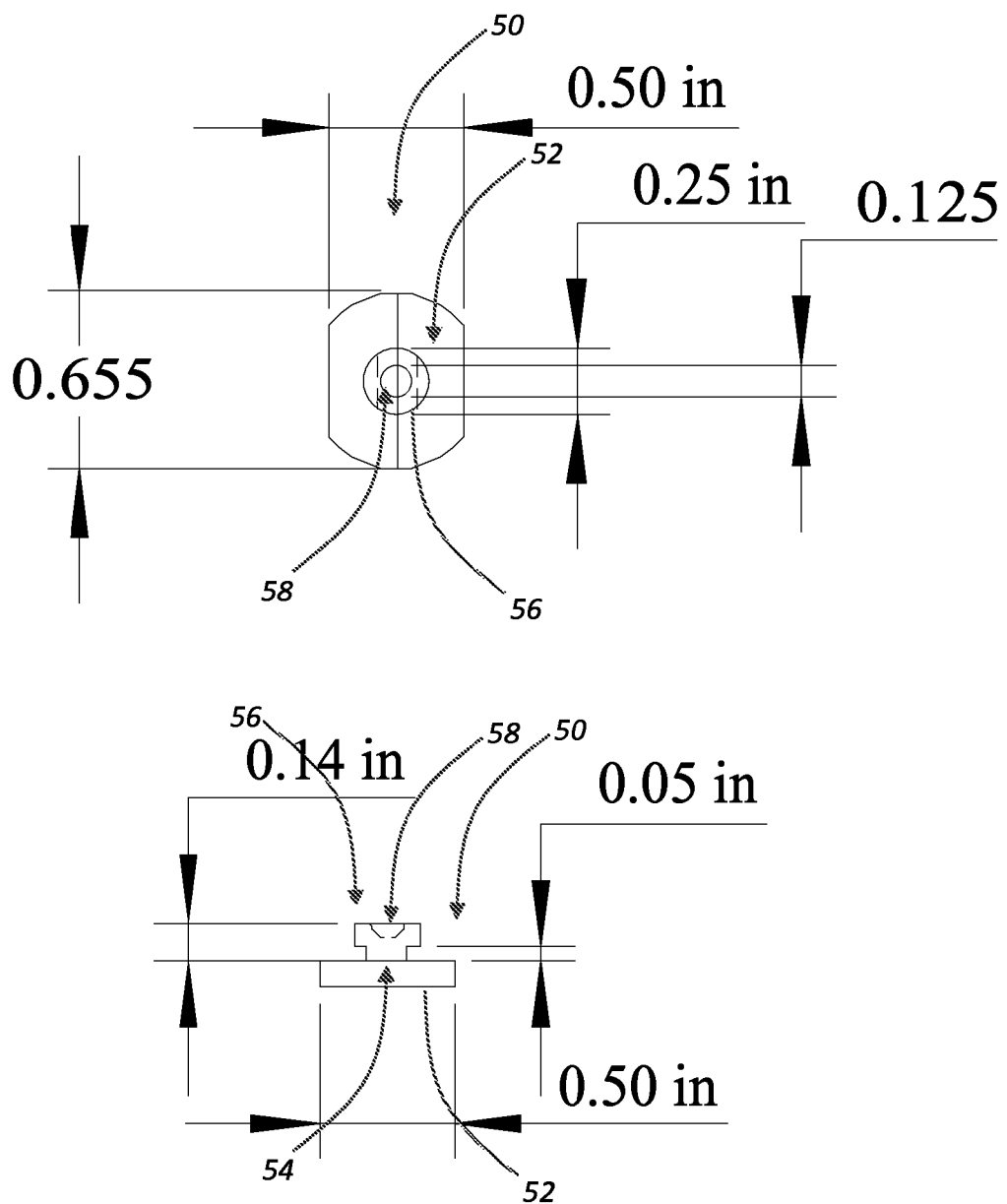
FIG. 3 is a series of planar views of one exemplary embodiment of a sample holding device that is selectively disposed within the environmental cell assembly of the present disclosure.

FIG. 3 shows one exemplary embodiment of a sample holding device 50 that is selectively disposed within the body assembly 12 (FIGS. 1 and 2) of the environmental cell assembly 10 (FIGS. 1 and 2) of the present disclosure. The sample holding device 50 is selectively disposed on the translating stage 32 (FIGS. 1 and 2), for example. In this exemplary embodiment, the sample holding device 50 includes a widened base portion 52, providing stability, a narrowed neck portion 54, configured to selectively receive a placement and removal tool 60 (FIG. 4), and a sample holding portion 56 including a concave recess 58 or the like, configured to selectively receive and retain the sample. Exemplary dimensions are provided in FIG. 3, but should not be construed to be limiting.

Figure 4:
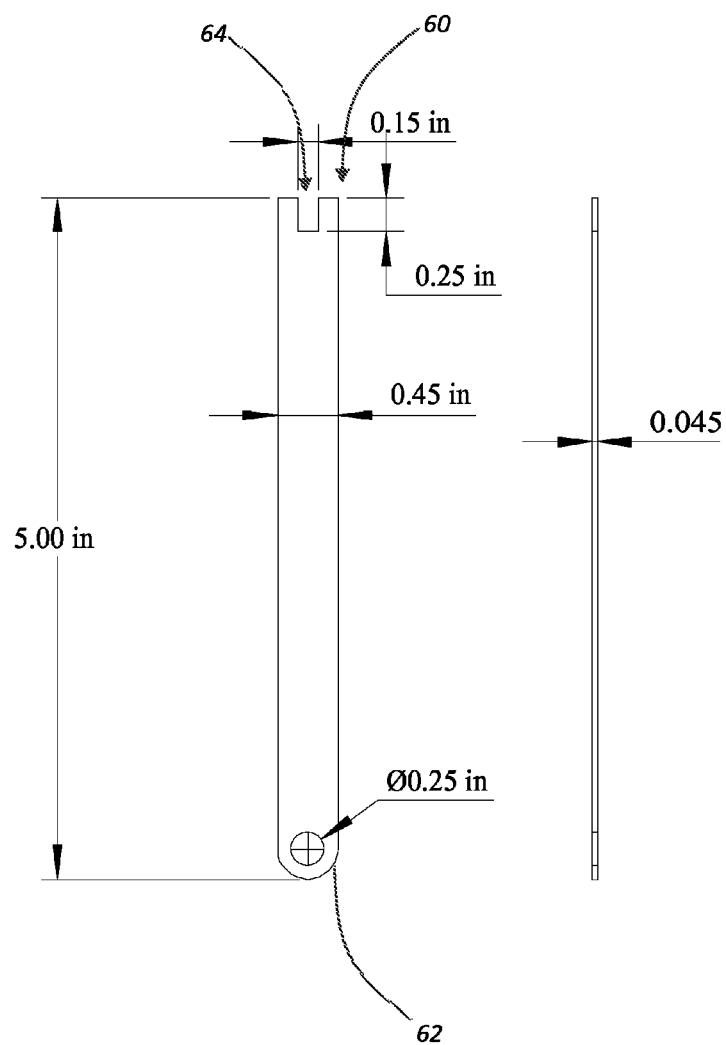
FIG. 4 is a series of planar views of one exemplary embodiment of a placement and removal tool for placing and removing the sample holding device of FIG. 3 within and from the environmental cell assembly of the present disclosure.

FIG. 4 shows one exemplary embodiment of the placement and removal tool 60 for placing and removing the sample holding device 50 (FIG. 3) within and from the body assembly 12 (FIGS. 1 and 2) of the environmental cell assembly 10 (FIGS. 1 and 2) of the present disclosure. In this exemplary embodiment, the placement and removal tool 60 includes an elongate portion 62 that can be grasped by a user and a recessed end portion 64 configured to engage the narrowed neck portion 54 (FIG. 3) of the sample holding device 50. Exemplary dimensions are provided in FIG. 4, but should not be construed to be limiting.

SPECIFIC IMPLEMENTATION

The environmental cell assembly 10 is constructed in the form of a cube with six ports. A modified microscope objective 28 is an integral part of the environmental cell assembly 10 and is placed in one port 26 and is sealed with double O-rings around the outside diameter of the objective 28. Any standard microscope objective (e.g. 0.85 in. diameter) of varying magnification can be utilized with the environmental cell assembly 10. The environmental cell assembly 10 is of such a size that it can be mounted in the objective turret by rotation with the objective 28, as would conventionally be done. The environmental cell assembly 10 possesses two viewing windows 36 mounted on two of the side ports 34, which can be assembled and disassembled from the environmental cell assembly 10 using standard conflat metal seals in order to load samples in a dry box environment. Two valves welded to conflat metal sealing plates are mounted on the other two side ports 24 for evacuation and/or purging with inert atmospheres. The bottom port 30 contains the sample holder mounted to a screw mechanism identical to that utilized on a 1.33" mini-confat commercial valve assembly, for example, that allows movement up and down from the outside the environmental cell assembly 10 for focusing a laser excitation source on the sample and the subsequent acquisition of a Raman spectrum once the environmental cell assembly 10 is mounted.

Although the present disclosure has been illustrated and described herein with reference to preferred embodiments and specific examples thereof, it will be appreciated by those of ordinary skill in the art that other embodiments and examples may perform similar functions and/or achieve like results. All such equivalent embodiments and examples are within the spirit and scope of the present disclosure, are contemplated thereby, and are intended to be covered by the following claims, which should be given the benefit of all reasonable equivalents.

What is claimed is:

1. An environmental cell assembly for use in microscopy and spectroscopy applications, comprising:
    an environmentally sealed body assembly configured to selectively hold a sample;
    a plurality of ports manufactured into one or more surfaces of the environmentally sealed body assembly for one or more of evacuating the environmentally sealed body assembly and injecting a gas into or removing a gas from the environmentally sealed body assembly;
    a port manufactured into a surface of the environmentally sealed body assembly for receiving a translating stage configured to move the sample within the environmentally sealed body assembly; and
    a port manufactured into a surface of the environmentally sealed body assembly for receiving one or more lenses utilized in a microscopy or spectroscopy application;
    wherein the one or more lenses are disposed adjacent the sample without intervening structures disposed there between.

2. The environmental cell assembly of claim 1, further comprising a port manufactured into a surface of the environmentally sealed body assembly for retaining a window and providing visualization of the sample.

3. The environmental cell assembly of claim 1, wherein the environmentally sealed body assembly comprises a plurality of sides that are one or more of fixedly attached to one another and integrally formed with one another.

4. The environmental cell assembly of claim 1, wherein the translating stage is operable for moving the sample vertically within the environmentally sealed body assembly.

5. The environmental cell assembly of claim 1, wherein the translating stage is operable for moving the sample horizontally within the environmentally sealed body assembly.

6. The environmental cell assembly of claim 1, further comprising a heating device disposed within or adjacent and in thermal communication with the environmentally sealed body assembly for selectively heating the sample.

7. The environmental cell assembly of claim 1, further comprising a sample holding device selectively disposed within the environmentally sealed body assembly.

8. A method for providing an environmental cell assembly for use in microscopy and spectroscopy applications, comprising:
    providing an environmentally sealed body assembly configured to selectively hold a sample;
    providing a plurality of ports manufactured into one or more surfaces of the environmentally sealed body assembly for one or more of evacuating the environmentally sealed body assembly and injecting a gas into or removing a gas from the environmentally sealed body assembly;
    providing a port manufactured into a surface of the environmentally sealed body assembly for receiving a translating stage configured to move the sample within the environmentally sealed body assembly; and
    providing a port manufactured into a surface of the environmentally sealed body assembly for receiving one or more lenses utilized in a microscopy or spectroscopy application;
    wherein the one or more lenses are disposed adjacent the sample without intervening structures disposed there between.

9. The method of claim 8, further comprising providing a port manufactured into a surface of the environmentally sealed body assembly for retaining a window and providing visualization of the sample.

10. The method of claim 8, wherein the environmentally sealed body assembly comprises a plurality of sides that are one or more of fixedly attached to one another and integrally formed with one another.

11. The method of claim 8, wherein the translating stage is operable for moving the sample vertically within the environmentally sealed body assembly.

12. The method of claim 8, wherein the translating stage is operable for moving the sample horizontally within the environmentally sealed body assembly.

13. The method of claim 8, further comprising providing a heating device disposed within or adjacent and in thermal communication with the environmentally sealed body assembly for selectively heating the sample.

14. The method of claim 8, further comprising providing a sample holding device selectively disposed within the environmentally sealed body assembly.

15. An environmental cell assembly for use in microscopy and spectroscopy applications, comprising:
   an environmentally sealed body assembly configured to selectively hold a sample;
   a plurality of ports manufactured into one or more surfaces of the environmentally sealed body assembly for one or more of evacuating the environmentally sealed body assembly and injecting a gas into or removing a gas from the environmentally sealed body assembly;
   a port manufactured into a surface of the environmentally sealed body assembly for receiving a translating stage configured to move the sample within the environmentally sealed body assembly; and
   a port manufactured into a surface of the environmentally sealed body assembly for receiving an objective utilized in a microscopy or spectroscopy application, wherein at least a portion of the objective protrudes into the environmentally sealed body assembly;
   wherein the one or more lenses are disposed adjacent the sample without intervening structures disposed there between.

16. The environmental cell assembly of claim 15, further comprising a port manufactured into a surface of the environmentally sealed body assembly for retaining a window and providing visualization of the sample.

17. The environmental cell assembly of claim 15, wherein the environmentally sealed body assembly comprises a plurality of sides that are one or more of fixedly attached to one another and integrally formed with one another.

18. The environmental cell assembly of claim 15, further comprising a heating device disposed within or adjacent and in thermal communication with the environmentally sealed body assembly for selectively heating the sample.

19. The environmental cell assembly of claim 15, further comprising a sample holding device selectively disposed within the environmentally sealed body assembly.

\* \* \* \* \*